United States Patent
Sugawara

(10) Patent No.: US 8,846,973 B2
(45) Date of Patent: Sep. 30, 2014

(54) PROCESS FOR PRODUCING HYDROGENATED AROMATIC POLYCARBOXYLIC ACID

(75) Inventor: Tomohiro Sugawara, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 902 days.

(21) Appl. No.: 13/055,247

(22) PCT Filed: Jul. 21, 2009

(86) PCT No.: PCT/JP2009/063055
§ 371 (c)(1),
(2), (4) Date: Apr. 28, 2011

(87) PCT Pub. No.: WO2010/010869
PCT Pub. Date: Jan. 28, 2010

(65) Prior Publication Data
US 2011/0196171 A1    Aug. 11, 2011

(30) Foreign Application Priority Data

Jul. 23, 2008 (JP) ................................ 2008-189832

(51) Int. Cl.
  *C07C 51/36* (2006.01)
  *C07C 61/09* (2006.01)
  *C07C 61/08* (2006.01)

(52) U.S. Cl.
  CPC .............. *C07C 51/36* (2013.01); *C07C 61/09* (2013.01); *C07C 61/08* (2013.01); *C07C 2101/14* (2013.01)
  USPC ....................................... 562/509

(58) Field of Classification Search
  CPC .... C07C 51/36; C07C 2101/14; C07C 61/08; C07C 61/09
  USPC ....................................... 562/509
  See application file for complete search history.

(56) References Cited

U.S. PATENT DOCUMENTS

| | | |
|---|---|---|
| 5,412,108 A | 5/1995 | Fisher |
| 2003/0149297 A1 | 8/2003 | Zaima |

FOREIGN PATENT DOCUMENTS

| | | |
|---|---|---|
| EP | 0 005 737 A1 | 12/1979 |
| EP | 1 323 700 A1 | 7/2003 |
| GB | 2 084 145 A | 4/1982 |
| JP | 57-53440 | 3/1982 |
| JP | 6-65165 | 3/1994 |
| JP | 8-325196 | 12/1996 |
| JP | 8-325201 | 12/1996 |
| JP | 2006-83080 | 3/2006 |
| JP | 2006-124313 | 5/2006 |
| JP | 2008-63263 | 3/2008 |

OTHER PUBLICATIONS

International Search Report issued Sep. 8, 2009 in PCT/JP2009/063055.
Extended European Search Report issued Nov. 27, 2012 in Patent Application No. 09800383.3.

*Primary Examiner* — Yevegeny Valenrod
(74) *Attorney, Agent, or Firm* — Oblon, Spivak, McClelland, Maier & Neustadt, L.L.P.

(57) ABSTRACT

A production method of a hydrogenated product of aromatic polycarboxylic acid by the hydrogenation of aromatic ring of the aromatic polycarboxylic acid in the presence of a catalyst composed of rhodium in combination with palladium and/or platinum supported on a carbon support. By using the catalyst, the hydrogenated product of aromatic polycarboxylic acid is produced industrially advantageously in high purity and high yield. By activating the catalyst composed of rhodium in combination with palladium and/or platinum supported on the carbon support after the hydrogenation, the conversion to the hydrogenated product of aromatic polycarboxylic acid is maintained at nearly 100% even after repeatedly using the catalyst many times. Also, a hydrogenated product of aromatic polycarboxylic acid substantially free from the starting aromatic polycarboxylic acid is obtained.

12 Claims, No Drawings

PROCESS FOR PRODUCING HYDROGENATED AROMATIC POLYCARBOXYLIC ACID

TECHNICAL FIELD

The present invention relates to a method of producing a hydrogenated product of aromatic polycarboxylic acid by the hydrogenation of the aromatic ring of the aromatic polycarboxylic acid (nuclear hydrogenation), and also relates to the hydrogenated product of aromatic polycarboxylic acid obtained by the method. More specifically, the present invention relates to a method of producing the hydrogenated product of aromatic polycarboxylic acid in high purity and high yield in industrial scale.

BACKGROUND ART

The hydrogenated product of aromatic polycarboxylic acid has been widely used as the raw material for functional polyimide and functional epoxy resin. With recent demand for more valuable functional resin, a hydrogenated product of aromatic polycarboxylic acid with high purity comes to be required. In particular, in an application field requiring high transparency, a hydrogenated product of aromatic polycarboxylic acid having the remaining amount of aromatic ring reduced as low as possible comes to be keenly demanded.

As the production method of a high-purity hydrogenated product of aromatic polycarboxylic acid, (i) a method of directly nuclear-hydrogenating an aromatic polycarboxylic acid (for example, Non-Patent Document 1 and Patent Documents 1 to 4) and (ii) a method in which an aromatic polycarboxylic acid is converted to its ester and then the ester is nuclear-hydrogenated (for example, Patent Documents 5 and 6) have been proposed.

Non-Patent Document 1 discloses (i) a method of nuclear-hydrogenating pyromellitic acid under a hydrogen pressure of 2.7 atm at 60° C. in the presence of a catalyst comprising 5% of rhodium metal supported on a carbon support (amount of rhodium metal used: 2% by weight of the starting compound) and (ii) a method of nuclear-hydrogenating phthalic acid, isophthalic acid, and terephthalic acid at 60 to 70° C. in the presence of a catalyst comprising 5% of rhodium metal supported on an alumina support (amount of rhodium metal used: 2.4% or 0.6% by weight of the starting compound).

Since a large amount of catalyst is used in both the methods mentioned above, the conversion and selectivity of the aromatic polycarboxylic acid are not necessarily sufficient and the starting aromatic polycarboxylic acid is likely to remain not hydrogenated.

Patent Document 1 proposes a method of nuclear-hydrogenating an aromatic polycarboxylic acid in the presence of a catalyst comprising rhodium metal and/or palladium metal in batchwise manner (amount of noble metal used: 0.5 to 10 parts by weight per 100 parts by weight of the aromatic polycarboxylic acid).

In the examples thereof, however, only the catalyst comprising 0.5% by weight, 2% by weight, or 5% by weight of rhodium supported on carbon and the catalyst comprising 5% by weight of palladium supported on carbon are used, and the nuclear hydrogenation in the presence of a catalyst comprising both rhodium and palladium is not described. The ability of reusing catalyst, which is important for industrial economy, is evaluated only by the reaction up to 9 times recycles.

Patent Document 2 proposes a method of nuclear-hydrogenating an aromatic polycarboxylic acid in the presence of a catalyst comprising 5% of rhodium metal supported on γ-alumina support having a specific surface area of 50 to 450 $m^2/g$ (amount of rhodium metal used: 0.25 part by weight or more and less than 0.5 part by weight per 100 parts by weight of the aromatic polycarboxylic acid).

Patent Document 2 describes that the reduction of catalyst activity is very small or hardly found even when the catalyst is continuously used in the nuclear hydrogenation without the activation treatment after every run of reaction (paragraph 0036). However, Patent Document 4 describes in comparative example 3 that when the nuclear hydrogenation is repeated using a catalyst comprising rhodium metal supported on γ-alumina support having a specific surface area of 150 $m^2/g$ without the activation treatment, the catalyst activity reduces and the conversion is extremely reduced in fourth run of the batchwise nuclear hydrogenation, thereby allowing a large amount of aromatic polycarboxylic acid to remain not hydrogenated. Therefore, the catalyst taught by Patent Document 2 does not endure the repeated use in a long period of time. In addition, it is economically very disadvantageous to change the highly expensive rhodium metal catalyst frequently for repeating the reaction.

Patent Document 3 proposes a method of nuclear-hydrogenating an aromatic polycarboxylic acid in the presence of a catalyst comprising one or more noble metals selected from ruthenium, rhodium, palladium, and platinum supported on an alumina, silica, or silica alumina support (amount of noble metal used: 0.05 to 0.45% by weight of the aromatic polycarboxylic acid).

However, only a rhodium alumina catalyst is used in the examples of Patent Document 3. The rhodium alumina catalyst is similar to the catalyst proposed by Patent Document 2. Like the catalyst of Patent Document 2, therefore, the rhodium alumina catalyst of Patent Document 3 is difficult to repeatedly use for a long period of time and economically disadvantageous.

Patent Document 4 describes that the decrease in the conversion and the degradation of catalyst can be prevented by conducting the nuclear hydrogenation at a limited range of temperature and further describes that the number of repeated use can be increased by an effective activation treatment.

In the examples of Patent Document 4, the rhodium catalyst is repeatedly used in the reaction. However, the number of repeated use is limited to about 10 times, and therefore, the catalyst is still economically disadvantageous.

Patent Documents 5 and 6 describe the method of converting an aromatic polycarboxylic acid to its ester and then nuclear-hydrogenating the ester.

However, the proposed method requires an additional step of converting the aromatic carboxylic acid to the ester, to elongate the overall production process and require a complicated reaction apparatus, thereby increasing production costs.

Patent Document 1: JP 2003-286222A
Patent Document 2: JP2006-83080A
Patent Document 3: JP2006-124313A
Patent Document 4: JP2008-63263A
Patent Document 5: JP8-325196A
Patent Document 6: JP8-325201A
Non-Patent Document 1: J. Org. Chem., 31, 3433 (1966)

DISCLOSURE OF THE INVENTION

An object of the present invention is to provide an industrially advantageous method of producing a hydrogenated product of aromatic polycarboxylic acid in high purity and high yield. Another object is to provide a hydrogenated product of aromatic polycarboxylic acid substantially free from the aromatic polycarboxylic acid which is used as the raw material.

As a result of extensive research in view of solving the above problems, the inventors have found that:
(1) by using a catalyst comprising rhodium in combination with palladium and/or platinum, the number of repeated use in the nuclear hydrogenation of an aromatic polycarboxylic acid is drastically increased as compared with using a catalyst consisting only one of the above metals, and
(2) by using the catalyst mentioned above, a hydrogenated product of aromatic polycarboxylic acid is produced in high purity and high yield.
The present invention is based on these findings.

Namely, the present invention relates to a production method of a hydrogenated product of aromatic polycarboxylic acid, which comprises a step of producing the hydrogenated product of aromatic polycarboxylic acid by hydrogenating an aromatic ring of the aromatic polycarboxylic acid in the presence of a catalyst and satisfies the following requirements (1) to (6):
(1) the catalyst is a supported catalyst comprising rhodium in combination with palladium and/or platinum supported on a carbon support;
(2) rhodium is used in an amount of 0.05 part by weight or more and less than 0.5 part by weight per 100 parts by weight of the aromatic polycarboxylic acid;
(3) palladium and/or platinum is used in an amount of 0.5 part by weight or more and less than 5.0 parts by weight per 100 parts by weight of the aromatic polycarboxylic acid;
(4) a hydrogen partial pressure is 1.0 to 15 MPa;
(5) a reaction temperature is 30 to 80° C.; and
(6) the aromatic polycarboxylic acid is dissolved or suspended in a reaction solvent.

BEST MODE FOR CARRYING OUT THE INVENTION

The aromatic polycarboxylic acid usable in the present invention is not particularly limited as long as the aromatic polycarboxylic acid has two or more carboxyl groups on its aromatic ring or rings, and selected from known aromatic polycarboxylic acids. Examples thereof include aromatic dicarboxylic acids, such as phthalic acid, isophthalic acid, terephthalic acid, 1,2-naphthalenedicarboxylic acid, 1,4-naphthalenedicarboxylic acid, 1,8-naphthalenedicarboxylic acid, 2,3-naphthalenedicarboxylic acid, 2,6-naphthalenedicarboxylic acid, 1,5-naphthalenedicarboxylic acid, 2,7-naphthalenedicarboxylic acid, 9,10-anthracenedicarboxylic acid, 4,4'-benzophenonedicarboxylic acid, 2,2'-biphenyldicarboxylic acid, 3,3'-biphenyldicarboxylic acid, 4,4'-biphenyldicarboxylic acid, 3,3'-biphenyl ether dicarboxylic acid, 4,4'-biphenyl ether dicarboxylic acid, and 4,4'-binaphthyldicarboxylic acid; aromatic tricarboxylic acids, such as hemimellitic acid, trimellitic acid, trimesic acid, 1,2,4-naphthalenetricarboxylic acid, and 2,5,7-naphthalenetricarboxylic acid; aromatic tetracarboxylic acids, such as mellophanic acid, prehnitic acid, pyromellitic acid, 3,3',4,4'-benzophenonetetracarboxylic acid, 2,2',3,3'-benzophenonetetracarboxylic acid, 2,3,3',4'-benzophenonetetracarboxylic acid, 3,3',4,4'-biphenyltetracarboxylic acid, 4, 4'-oxydiphthalic acid, 3,3',4,4'-diphenylmethanetetracarboxylic acid, 1,4,5,8-naphthalenetetracarboxylic acid, 2,3,6,7-naphthalenetetracarboxylic acid, and anthracenetetracarboxylic acid; aromatic pentacarboxylic acids, such as benzenepentacarboxylic acid; and aromatic hexacarboxylic acids, such as benzenehexacarboxylic acid. These acids may be used alone or in combination of two or more.

Of the above, the aromatic tricarboxylic acid and aromatic tetracarboxylic acid are preferred. Specifically, trimellitic acid, hemimellitic acid, trimesic acid, pyromellitic acid, 1,4,5,8-naphthalenetetracarboxylic acid, 2,3,6,7-naphthalenetetracarboxylic acid, and 3,3',4,4'-biphenyltetracarboxylic acid are preferred, and trimellitic acid, hemimellitic acid, trimesic acid, and pyromellitic acid are more preferred. These acids may be used alone or in combination of two or more.

In the present invention, the hydrogenated product of aromatic polycarboxylic acid is produced by the hydrogenation of the aromatic ring in the aromatic polycarboxylic acid (nuclear hydrogenation) in the presence of the catalyst. When the starting aromatic polycarboxylic acid has two or more aromatic rings, the hydrogenated product of aromatic polycarboxylic acid may be a completely hydrogenated product (all the aromatic rings are hydrogenated) or a partly hydrogenated product (part of the aromatic rings are hydrogenated). Examples of the partly hydrogenated product include a compound having a tetralin structure when the starting aromatic polycarboxylic acid has a naphthalene structure; and a compound having a benzene ring and a cyclohexane ring when the starting aromatic polycarboxylic acid has a biphenyl structure or two benzene rings bonding via a linking group of various type.

Examples of the hydrogenated product of aromatic polycarboxylic acid include 1,2,4-cyclohexanetricarboxylic acid, 1,2,3-cyclohexanetricarboxylic acid, 1,3,5-cyclohexanetricarboxylic acid, 1,2,4,5-cyclohexanetetracarboxylic acid, 1,4,5,8-decahydronaphthalenetetracarboxylic acid, 2,3,6,7-decahydronaphthalenetetracarboxylic acid, and 3,3',4,4'-bicyclohexyltetracarboxylic acid.

The nuclear hydrogenation reaction of the present invention is preferably conducted in a reaction solvent. Examples of the reaction solvent include water, acetic acid, propionic acid, dimethyl ether, methyl ethyl ether, methyl acetate, ethyl acetate, propyl acetate, tetrahydrofuran, acetone, methyl ethyl ketone, ethylene glycol dimethyl ether, diethylene glycol dimethyl ether, and triethylene glycol dimethyl ether, with water being preferred. Ion-exchanged water and distilled water are preferably used. When a hydrogenated product of aromatic polycarboxylic acid is to be used in electric or electronic application field is intended, water containing metals, such as sodium, potassium, calcium, magnesium, and iron, in a content as low as possible is preferably used.

The use of water as the reaction solvent has the following advantages:
(i) the nuclear hydrogenation proceeds easily because the aromatic polycarboxylic acid easily dissolves in water;
(ii) the obtained hydrogenated product of aromatic polycarboxylic acid is easily separated from the catalyst because it easily dissolves in water; and
(iii) the operations such as separation and recovery after the nuclear hydrogenation are easy because the hydrogenated product of aromatic polycarboxylic acid with high purity are obtained by separating the catalyst, crystallizing the hydrogenated product of aromatic polycarboxylic acid by concentrating or cooling the filtrate, and solid-liquid separating the crystallized product by filtration or centrifugation.

The starting aromatic polycarboxylic acid may be dissolved or suspended in the reaction solvent. The concentration of the aromatic polycarboxylic acid is preferably 5 to 40% by weight and more preferably 10 to 40% by weight based on the total weight of the aromatic polycarboxylic acid and the reaction solvent.

After the nuclear hydrogenation, the hydrogenated product of aromatic polycarboxylic acid is crystallized by cooling or concentration and the crystals are separated. The mother liquor after separating the crystals may be recycled for reuse as the reaction solvent. The amount of the mother liquor to be recycled to the reaction apparatus can be determined according to the content of accumulated impurities in the reaction system.

The nuclear hydrogenation is conducted in the presence of a catalyst comprising rhodium in combination with palladium and/or platinum which are supported on a carbon support, with a catalyst comprising rhodium and palladium supported on a carbon support being particularly preferred. The form of catalyst is not particularly limited, and a powdery catalyst, a crushed or pelletized catalyst for fixed bed and catalysts with other forms are used according to the manner of hydrogenation reaction. The supported amount of each of the above noble metals on the support is preferably 0.5 to 10% by weight and more preferably 2 to 5% by weight based on the total amount of catalyst. Catalysts each being composed of only one kind of noble metal supported on carbon may be used in mixture. A catalyst composed of two or more noble metals supported simultaneously on the support is also usable.

As compared with using the catalyst composed of only one kind of metal, by using the Catalyst comprising rhodium in combination with palladium and/or platinum which are simultaneously supported on the support or a mixture of catalysts each being composed of only one of the above metals, the formation of a by-product in which the carboxyl group of the starting aromatic polycarboxylic acid is converted to methyl group is prevented. In addition, the specific isomer of the hydrogenated product of aromatic polycarboxylic acid is obtained in a good selectivity and nearly pure form. The hydrogenated product of aromatic polycarboxylic acid thus obtained is easily handled in the production of a functional polymer, etc. and provides the aimed product with high purity.

The nuclear hydrogenation of the invention is preferably conducted under a hydrogen partial pressure of 1.0 MPa or more under stirring in the presence of a catalyst containing rhodium in 0.05 part by weight or more and less than 0.5 part by weight, preferably 0.1 part by weight or more and less than 0.5 part by weight, and more preferably 0.13 part by weight or more and less than 0.5 part by weight and further containing palladium and/or platinum in 0.5 part by weight or more and less than 5.0 parts by weight, each based on 100 parts by weight of the aromatic polycarboxylic acid. If the amount of the noble metal is less than the above range, the nuclear hydrogenation may proceed not sufficiently. Even if more than the above range, additional effect corresponding to a larger amount is hardly obtained, thereby likely to increase production costs. If the hydrogen partial pressure is less than 1.0 MPa, the intended conversion is not obtained, thereby failing to achieve the object of the invention. The hydrogen partial pressure is preferably 1.0 to 15 MPa. The reaction temperature is preferably 30 to 80° C. and more preferably 50 to 65° C.

An industrially general grade of hydrogen gas is sufficient for the invention, for example, hydrogen gas with 99.9% or more purity produced by PSA method or a membrane hydrogen production method is usable.

Since the nuclear hydrogenation is exothermic, the temperature of the reaction system rises at the initial stage of the reaction. Since the reaction heat is scarcely generated at the final stage of the reaction, the temperature of the reaction system lowers because of radiation of heat from the production apparatus. Therefore, it is preferred to regulate the variation of the reaction temperature within ±5° C. of the temperature initially set by cooling or heating the reaction system using a heating or cooling device according to the degree of heat generation and heat radiation from the production apparatus. By regulating the variation of the reaction temperature within ±5° C., the use of an excessive amount of catalyst is avoided and the conversion of the raw material is maintained at nearly 100% even after using the catalyst repeatedly many times.

Any of the heating reaction apparatuses generally used may be used in the present invention. Preferred heating methods are, for example, an internal coil heating method in which coil for passing a heating medium through it is disposed in a reaction apparatus; a jacket heating method in which a heating medium is passed along the outer surface of a reaction apparatus; and a heating method with external circulation in which a portion of reaction liquid is pumped into an external path and heated by a heat exchanger. Examples of the heating medium include steam and hot oil. Preferred cooling methods are, for example, an internal coil cooling method in which coil for passing a cooling medium through it is disposed in a reaction apparatus; a jacket cooling method in which a cooling medium is passed along the outer surface of a reaction apparatus; and a cooling method with external circulation in which a portion of reaction liquid is pumped into an external path and cooled by a heat exchanger. Examples of the cooling medium include cooled water and ethanol.

The reaction time depends on the reaction temperature and other reaction conditions and is not determined absolutely. Generally, a reaction time of about 0.5 to 3 h is sufficient The catalyst used in the nuclear hydrogenation is separated from the reaction product mixture by filtration, etc. and the separated catalyst can be repeatedly reused after the activation treatment. The method of activating the catalyst may include a method of contacting with air, a method of treating with an oxidizing agent, a method of contacting with nitrogen gas, a method of treating with steam, and a method of treating with aqueous solution of alkali. In the method of contacting with air, the separated catalyst placed in a glass container, etc. is allowed to stand in air for several hours or longer (for example, 1 to 100 h at 0 to 100° C.), or air is bubbled through a slurry of 10 to 50 parts by weight of catalyst in 100 ml of water (ion-exchanged water or distilled water) at a rate of 1 to 1000 ml/min at 0 to 100° C. for 0.1 to 10 h under stirring. Example of the oxidizing agent includes hydrogen peroxide. Examples of the aqueous solution of alkali include a 0.5 to 10% by weight aqueous solution of sodium hydroxide and a 0.5 to 10% by weight aqueous ammonia. The treatment with alkali is conducted, for example, by stirring a mixture of 10 to 50 parts by weight of the catalyst in 100 parts by weight of an aqueous solution of alkali at 0 to 100° C. for 0.1 to 10 h. The catalyst treated with alkali is preferably washed with a lower aliphatic carboxylic acid, such as acetic acid, and finally with water to reduce the remaining alkali as low as possible.

Of the above activation methods, the method of contacting with air, the method of treating with an aqueous solution of alkali, and a combination thereof are preferred in view of the activation effect, etc.

The reaction apparatus for the nuclear hydrogenation is not particularly limited and a known apparatus is usable as long as the apparatus is (i) made of a material resistant to acids, (ii) pressure-resistant, and (iii) equipped with a stirring device capable of sufficiently mixing the catalyst, the aromatic polycarboxylic acid and hydrogen. For example, a SUS316L vertical or horizontal autoclave is usable.

The reaction manner of the nuclear hydrogenation is not particularly limited as long as the effect of the invention is not adversely affected. For example, the nuclear hydrogenation may be conducted by charging the starting material, the reaction solvent and the catalyst, each in a predetermined amount, into an apparatus, replacing the reaction system with an inert gas and then with hydrogen gas, and allowing the nuclear hydrogenation to proceed under predetermined reaction conditions (hydrogen partial pressure, reaction temperature, reaction time, stirring speed, etc.).

After the reaction, the aimed hydrogenated product of aromatic polycarboxylic acid is obtained, for example, by filtering off the catalyst at a temperature near the reaction temperature, cooling the filtrate to room temperature; separating the precipitated solid by filtration, and drying the separated solid.

The aimed hydrogenated product of aromatic polycarboxylic acid is also obtained by evaporating off the reaction solvent to concentrate the filtrate, separating the precipitated solid by filtration, and drying the separated solid.

When a relatively large amount of the hydrogenated product of aromatic polycarboxylic acid precipitates at the completion of the nuclear hydrogenation or when the hydrogenated product of aromatic polycarboxylic acid is expected to precipitate during the removal of the catalyst, the filtration temperature may be raised or the reaction solvent may be added. It is recommended to add the reaction solvent to the reaction product liquid after the nuclear hydrogenation is completed and prior to the subsequent operations if the viscosity of the system increases as the hydrogenated product precipitates.

By the production method of the invention mentioned above, the hydrogenated product of aromatic polycarboxylic acid containing the starting aromatic polycarboxylic acid in a remaining amount of 0.10% by weight or less, and preferably in an extremely small amount or is free from it is produced by a simple process in an industrially advantageous manner. The words "in an extremely small amount or is free from it" mean that the remaining amount of the aromatic polycarboxylic acid in the hydrogenated product of aromatic polycarboxylic acid is the detection limit or less when analyzed by gas chromatography.

EXAMPLES

The present invention will be described in details with reference to the examples and comparative examples. However, it should be noted that the scope of the present invention is not limited to the following examples.
Conditions of Gas Chromatographic Analysis
Pre-Treatment
A sample was dissolved in diethylene glycol dimethyl ether in a solid concentration of 6% by weight. The solution was subjected to methyl esterification by adding diazomethane to prepare the sample solution for gas chromatography. The injection amount was 0.8 µL.
Conditions of Gas Chromatographic Analysis
  Apparatus: GC-17A (manufactured by Shimadzu Corporation)
  Capillary column: DB-1 (manufactured by Shimadzu Corporation)
  Injection temperature: 300° C.
  Detector temperature: 280° C.
  Initial column temperature and retention time: 200° C. and 10 min
  Temperature raising speed: 7° C./min
  Final column temperature and retention time: 280° C. and 40 min
  Carrier gas: helium
  Carrier gas pressure: 130 kPa
  Detector: FID Example 1

The following compound, catalyst, and reaction solvent were charged in a 500-ml SUS316L shaking autoclave equipped with a stirrer, a thermometer, a pressure gauge, an inlet tube, and a heating/cooling device which allows a cooling water and steam to pass through it.
  20 g of pyromellitic acid;
  80 g of ion-exchanged water;
  4.0 g of 5% by weight rhodium-carbon supported catalyst (manufactured by N.E. Chemcat Corporation, water-containing catalyst, water content: 50.5% by weight, amount of rhodium metal: less than 0.5 part by weight per 100 parts by weight of pyromellitic acid); and
  36 g of 5% by weight palladium-carbon supported catalyst (manufactured by N.E. Chemcat Corporation, water-containing catalyst, water content: 50.5% by weight, amount of palladium metal: about 4.5 parts by weight per 100 parts by weight of pyromellitic acid).

The reaction system was replaced with nitrogen gas twice while stirring the contents. Then, after replacing with hydrogen gas fives times, the pressure was raised to 8 MPa. The reaction was allowed to proceed at 60° C. while keeping the hydrogen partial pressure at 8 MPa. The reaction system was cooled at the initial stage of the reaction so that the temperature did not exceed 65° C. clue to the reaction heat. After one hour of the reaction where the reaction heat was little generated, the reaction system was heated by steam so that the temperature was not lower than 55° C.

After two hours from the replacement with hydrogen gas, the reaction product liquid was taken from the autoclave through the tube equipped with a filter under pressure of nitrogen gas and the catalyst was filtered off to obtain a colorless transparent filtrate. The filtrate (crude reaction product) was gas-chromatographically analyzed. The results are shown in Table 1. The conversion of pyromellitic acid (PMA) was 99.92% by weight, the selectivity of 1,2,4,5-cyclohexanetetracarboxylic acid (HPMA) was 99.01% by weight, and the selectivity of by-product (Me-HTMA: 1,2,4,5-cyclohexanetetracarboxylic acid having one of its carboxyl groups converted to methyl group) was 0.65% by weight. The reaction yield of HPMA was 98.93% by weight. The content of the isomer (HPMA-5) represented by the following formula (1) in HPMA was 97.09% by weight.

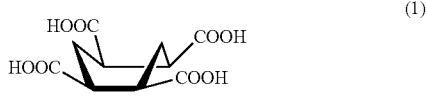

(1)

Then, the filtrate was concentrated by a rotary evaporator under reduced pressure to allow 1,2,4,5-cyclohexanetetracarboxylic acid (HPMA) to crystallize. The crystals were separated and dried to obtain 16.37 g of dried crystals. The dried crystals was analyzed by gas chromatography, the results of which are shown in Table 1. The purity of HPMA was 99.10% by weight and the starting pyromellitic acid was not detected therein (detection limit: 0.02% by weight).

Example 2

130 Repeated Activations by Air

The mixture of carbon supported catalysts filtered off in Example 1 was added with 100 ml of ion-exchanged water. Air was blown into the obtained aqueous slurry for 1.5 h at a rate of 18 ml/min while stirring by the stirrer at room temperature, to activate the catalysts by air. Immediately after the separation by filtration, the mixture of carbon supported catalysts was charged in the autoclave together with 20 g of pyromellitic acid and 80 g of ion-exchanged water, and the nuclear hydrogenation was conducted in the same manner as in Example 1. Thereafter, the cycle composed of the separation of the mixture of carbon supported catalysts, the activation by air and the nuclear hydrogenation sequentially was repeated 130 times to conduct the recycling test of catalyst. The results of analyzing the filtrate (crude reaction product) obtained in the 131st run of the nuclear hydrogenation are shown in Table 1. From the results, it was found that the reduction in the catalyst activity was very small. In the same manner as in Example 1, 15.96 g of dried crystals of 1,2,4,5-cyclohexanetetracarboxylic acid were obtained. The results of analyzing the dried crystals are shown in Table 1.

Example 3

The nuclear hydrogenation, the post-treatments and the analysis were conducted in the same manner as in Example 1, except for using 600 parts by weight of ion-exchanged water, 5% by weight rhodium-carbon supported catalyst in an amount corresponding to 0.15 part by weight of rhodium metal and 5% by weight palladium-carbon supported catalyst in an amount corresponding to 1.35 parts by weight of palladium metal each based on 100 parts by weight of pyromellitic acid, and changing the reaction temperature to 40° C. The results are shown in Table 1.

Example 4

97 Repeated Activations by Air

The cycle composed of the separation of the mixture of carbon supported catalysts, the activation by air and the nuclear hydrogenation was repeated 97 times in the same manner as in Example 2 to conduct the recycling test of catalyst, except for conducting each run of the nuclear hydrogenations in the same manner as in Example 3. The results are shown in Table 1.

Comparative Example 1

The nuclear hydrogenation, the analysis of the filtrate (crude reaction product), and the post-treatments were conducted in the same manner as in Example 1, except for using 4.0 g of 5% by weight rhodium-carbon supported catalyst (less than 0.5 part by weight of rhodium metal per 100 parts by weight of pyromellitic acid) alone and changing the reaction temperature to 50° C., thereby obtaining 16.16 g of dried crystals. The results of the analysis are shown in Table 1. It was found that as compared with Example 1 Me-HTMA was formed in a large amount and the yield of 1,2,4,5-cyclohexanetetracarboxylic acid was low. In addition, the content of HPMA-5 was extremely low (extremely low selectivity of the isomer).

Comparative Example 2

11 Repeated Activations by Air

The rhodium-carbon supported catalyst recovered by separation in Comparative Example 1 was added with 100 ml of ion-exchanged water. Air was blown into the obtained aqueous slurry for 1.5 h at a rate of 18 ml/min while stirring by the stirrer, to activate the catalyst by air. Immediately after the separation by filtration, the rhodium-carbon supported catalyst was charged in the autoclave together with 20 g of pyromellitic acid and 80 g of ion-exchanged water, and the nuclear hydrogenation was conducted in the same manner as in Example 1. Thereafter, the cycle composed of the separation of the rhodium-carbon supported catalyst, the activation by air and the nuclear hydrogenation was repeated 11 times to conduct the recycling test of catalyst. The results of analyzing the filtrate (crude reaction product) obtained in the 12th run of the nuclear hydrogenation are shown in Table 1. From the results, it can be seen that the catalyst activity is extremely lowered, although the catalyst was reused only less than 1/10 of the reused number of Example 2. The post-treatments were conducted in the same manner as in Comparative Example 1, to obtain 15.96 g of dried crystals. The results of analysis thereof are shown in Table 1. The purity of the dried crystals of 1,2,4,5-cyclohexanetetracarboxylic acid was low because of a large amount of the starting pyromellitic acid remained therein.

Comparative Example 3

The nuclear hydrogenation, the analysis of the filtrate (crude reaction product), and the post-treatments were conducted in the same manner as in Example 1, except for using 40 g of 5% by weight palladium-carbon supported catalyst (less than 5.0 parts by weight of palladium metal per 100 parts by weight of pyromellitic acid) alone and changing the reaction temperature to 50° C., thereby obtaining 16.16 g of dried crystals. The results of the analysis are shown in Table 1. It was found that as compared with Example 1 the content of HPMA-5 was extremely low (extremely low selectivity of the isomer).

Comparative Example 4

35 Repeated Activations by Air

The palladium-carbon supported catalyst recovered by separation in. Comparative Example 3 was added with 100 ml of ion-exchanged water. Air was blown into the obtained aqueous slurry for 1.5 h at a rate of 18 ml/min while stirring by the stirrer, to activate the catalyst by air. Immediately after the separation by filtration, the palladium-carbon supported catalyst was charged in the autoclave together with 20 g of pyromellitic acid and 80 g of ion-exchanged water, and the nuclear hydrogenation was conducted in the same manner as in Example 1. Thereafter, the cycle composed of the separation of the palladium-carbon supported catalyst, the activation by air and the nuclear hydrogenation was repeated 35 times to conduct the recycling test of catalyst. The results of analyzing the filtrate (crude reaction product) obtained in the 36th run of the nuclear hydrogenation are shown in Table 1.

From the results, it can be seen that the catalyst activity was extremely lowered, although the catalyst was reused only about ¼ of the reused number of Example 2. The post-treatments were conducted in the same manner as in Comparative Example 1, to obtain 15.96 g of dried crystals. The results of analysis thereof are shown in Table 1. The purity of the dried crystals of 1,2,4,5-cyclohexanetetracarboxylic acid was low because of a large amount of the starting pyromellitic acid remained therein.

TABLE 1

|  | Number of reusing catalyst | Crude reaction product | | | | | Dried Crystal | |
|---|---|---|---|---|---|---|---|---|
|  |  | PMA Conversion (% by weight) | HPMA Selectivity (% by weight) | Me-HTMA Selectivity (% by weight) | HPMA Yield (% by weight) | HPMA-5/ HPMA (% by weight) | HPMA Purity (% by weight) | PMA (% by weight) |
| Examples | | | | | | | | |
| 1 | 0 | 99.92 | 99.01 | 0.65 | 98.93 | 97.09 | 99.10 | 0.00 |
| 2 | 130 | 98.97 | 96.16 | 3.01 | 95.17 | 96.59 | 98.75 | 0.00 |
| 3 | 0 | 99.59 | 98.53 | 1.15 | 98.13 | 96.35 | 99.20 | 0.00 |
| 4 | 97 | 99.14 | 96.96 | 2.59 | 96.13 | 97.51 | 98.83 | 0.00 |
| Comparative Examples | | | | | | | | |
| 1 | 0 | 99.65 | 96.49 | 3.60 | 96.15 | 93.67 | 99.08 | 0.00 |
| 2 | 11 | 94.96 | 95.51 | 4.05 | 90.70 | 93.21 | 84.75 | 14.65 |
| 3 | 0 | 99.96 | 99.15 | 0.46 | 99.11 | 91.67 | 99.09 | 0.00 |
| 4 | 35 | 95.53 | 94.36 | 4.14 | 90.14 | 89.90 | 85.90 | 13.50 |

PMA: pyromellitic acid.
HPMA: 1,2,4,5-cyclohexanetetracarboxylic acid.
Me-HTMA: by-product wherein one of the carboxyl groups of HPMA was converted to methyl group.
HPMA-5: isomer of HPMA represented by formula (1).

INDUSTRIAL APPLICABILITY

According to the present invention, the hydrogenated product of aromatic polycarboxylic acid is produced in high purity and high yield in industrially advantageous manner. The hydrogenated product of aromatic polycarboxylic acid produced by the production method of the invention contains the starting aromatic polycarboxylic acid in an extremely small amount or is substantially free from it. Therefore, the hydrogenated product is useful as the raw monomer for the production of a transparent solvent-soluble functional polymer or polyester and as the raw material for a curing agent of a transparent functional epoxy resin.

What is claimed is:

1. A method of producing a hydrogenated product of aromatic polycarboxylic acid, the method comprising:
   producing the hydrogenated product of the aromatic polycarboxylic acid by hydrogenating an aromatic ring of the aromatic polycarboxylic acid in the presence of a catalyst,
   wherein:
   (1) the catalyst is a supported catalyst comprising rhodium in combination with palladium supported on a carbon support;
   (2) the rhodium is present in an amount of 0.05 part by weight or more and less than 0.5 part by weight per 100 parts by weight of the aromatic polycarboxylic acid;
   (3) the palladium is present in an amount of 0.5 part by weight or more and less than 5.0 parts by weight per 100 parts by weight of the aromatic polycarboxylic acid;
   (4) a hydrogen partial pressure is 1.0 to 15 MPa;
   (5) a reaction temperature is 30 to 80° C.; and
   (6) the aromatic polycarboxylic acid is dissolved or suspended in a reaction solvent.

2. The method according to claim 1, wherein the reaction temperature is 50 to 65° C.

3. The method according to claim 1, wherein the catalyst is activated after the hydrogenating.

4. The method according to claim 3, wherein the catalyst is activated by
   bringing the catalyst into contact with air,
   treating the catalyst with an aqueous solution of alkali, or a combination thereof.

5. The method according to claim 1, wherein a concentration of the aromatic polycarboxylic acid is 5 to 40% by weight based on a total amount of the aromatic polycarboxylic acid and the reaction solvent.

6. The method according to claim 1, wherein the reaction solvent is water.

7. The method according to claim 1, wherein the aromatic polycarboxylic acid is at least one compound selected from the group consisting of trimellitic acid, hemimellitic acid, trimesic acid, and pyromellitic acid.

8. The method according to claim 2, wherein the catalyst is activated after the hydrogenating.

9. The method according to claim 8, wherein the catalyst is activated by
   bringing the catalyst into contact with air,
   treating the catalyst with an aqueous solution of alkali, or a combination thereof.

10. The method according to claim 2, wherein a concentration of the aromatic polycarboxylic acid is 5 to 40% by weight based on a total amount of the aromatic polycarboxylic acid and the reaction solvent.

11. The method according to claim 3, wherein a concentration of the aromatic polycarboxylic acid is 5 to 40% by weight based on a total amount of the aromatic polycarboxylic acid and the reaction solvent.

12. The method according to claim 4, wherein a concentration of the aromatic polycarboxylic acid is 5 to 40% by weight based on a total amount of the aromatic polycarboxylic acid and the reaction solvent.

* * * * *